United States Patent [19]

Okazaki

[11] Patent Number: 4,508,449
[45] Date of Patent: Apr. 2, 1985

[54] APPARATUS FOR MEASURING DIAMOND COLORS

[75] Inventor: Nobuo Okazaki, Nagaokakyo, Japan

[73] Assignee: Shimadzu Corporation, Kyoto, Japan

[21] Appl. No.: 389,977

[22] Filed: Jun. 18, 1982

[30] Foreign Application Priority Data

Jun. 25, 1981 [JP] Japan .................................. 56-99228

[51] Int. Cl.³ .............................................. G01J 3/50
[52] U.S. Cl. ...................................... 356/30; 356/244
[58] Field of Search ........................... 356/30, 236, 244

[56] References Cited

U.S. PATENT DOCUMENTS 3,867,032 2/1975 Bruck ...................................... 356/30
4,310,249 1/1982 Kramer ........................... 356/236 X

FOREIGN PATENT DOCUMENTS 2036360 6/1980 United Kingdom ................... 356/30

Primary Examiner—F. L. Evans
Attorney, Agent, or Firm—Hubbell, Cohen, Stiefel & Gross

[57] ABSTRACT

An apparatus for measuring the color of a brilliant-cut diamond, comprising a light source for providing a measuring light, a holder for holding the diamond to allow the measuring light to enter the diamond through a table facet thereof, a photodetector for detecting a light which has emerged from the diamond through its table facet, a measurement unit for measuring a spectrum of the detected light and an arithmetic unit for deriving tristimulus values from the spectrum.

The apparatus is of great practical advantage in that it can objectively measure the colors of brilliant-cut diamonds, and can produce measured outputs which can easily be converted to color grades of the type which has widely been used conventionally.

3 Claims, 8 Drawing Figures

1

APPARATUS FOR MEASURING DIAMOND COLORS

BACKGROUND OF THE INVENTION

1. Field of the Invention

The present invention relates to an apparatus for measuring diamond colors, and more particularly to such an apparatus for measuring the spectrum of a beam of light that has passed through a diamond, deriving tristimulus values X, Y and Z from the measured spectrum, and evaluating the color grade of the diamond.

2. Description of the Prior Art

Diamonds are normally evaluated by the qualities of "4C": color, clarity, carat, and cutting. Color determination has heretofore been conducted by an organoleptic examination in which the hue of yellow is classified by human eyes into grades ranging from water-whiteness to light yellow for evaluation.

The organoleptic color determination however lacks objectivity no matter how skilled the observer may be. It frequently occurs in reality that a diamond color is differently judged by different observers. Proper determination of diamond colors is more desired since diamonds are getting more and more popular among people and their market is expanding. There has been a need for apparatus for properly measuring diamond colors without resorting to subjectified judgement by human observers.

SUMMARY OF THE INVENTION

The present inventor has made various studies and reached the following findings:

(a) Ordinary spectrophotometry fails to measure the spectrum of a light having passed through a diamond with an ultra-multiplicity of facets. The spectrum of a light which has passed through a diamond with a brilliant cut can however be properly obtained by directing a measuring light to the table facet side of the diamond, and measuring the light which has been reflected many times within the diamond and has emerged through the table facet side.

The term "measuring light" means a white light which has a wavelength in the range of from about 380 to about 780 nm or a monochromatic light which varies its wavelength in said range.

The term "the table facet side" as used herein means that it includes at least the table facet of the brilliant cut diamond, and optionally includes crown facets adjacent to said table facet.

(b) Where tristimulus values X, Y and Z are calculated from the spectrum and corresponding positions are found on a chromaticity diagram, such positions are correlated to the conventional color determination based on the organoleptic examination.

(c) Measurement accuracy is improved by measuring a spectrum while a diamond of a brilliant cut is being rotated, rather than fixed, about an axis passing through the center of the table and culet of the diamond.

Based on the above findings, the inventor has made the present invention which provides an effective apparatus for objectively determining diamond colors.

According to the present invention, there is provided an apparatus for measuring the color of a diamond, comprising a light source, a holder for holding the diamond on its pavillion to allow a measuring light emitted from the light source to enter the diamond thru the table facet side thereof, a photodetector for detecting a light which has emerged from the diamond thru the table facet side, a measurement unit for controlling a monochromator included in at least one of the light source and the photodetector to obtain a spectrum of the detected light having passed through the diamond, and an arithmetic unit for deriving tristimulus values X, Y and Z from the measured spectrum.

According to the present invention, there is also provided an apparatus for measuring the color of a diamond with a brilliant cut, comprising a light source for providing a measuring light, a rotatable holder for holding the diamond on its pavillion to allow the measuring light to enter the diamond thru the table facet side thereof while rotating the diamond about an axis passing thru the center of the table and the culet of the diamond, a photodetector for detecting a light which has emerged from the diamond thru the table facet side, a measurement unit for controlling a monochromator included in at least one of the light source and the photodetector to obtain a spectrum of the detected light, and an arithmetic unit for deriving tristimulus values X, Y and Z from the measured spectrum.

According to another aspect of the invention, there is provided a method of measuring the color of a diamond, comprising the steps of: irradiating the table facet side of a brilliant-cut diamond with a measuring light, obtaining the spectrum of light which has passed through the diamond, deriving tristimulus values X, Y and Z from the spectrum based on the following known equations (I), (II) and (III):

$$X = K \int \psi(\lambda) \overline{X}(\lambda) d\lambda \qquad (I)$$

$$Y = K \int \psi(\lambda) \overline{Y}(\lambda) d\lambda \qquad (II)$$

$$Z = K \int \psi(\lambda) \overline{Z}(\lambda) d\lambda \qquad (III)$$

where $\psi(\lambda)$ is the spectrum, $\overline{X}(\lambda)$, $\overline{Y}(\lambda)$ and $\overline{Z}(\lambda)$ are the color matching functions, and K is a constant for equalizing Y to the amount of the measured light, and then defining the color grade of the diamond based on the values X, Y and Z.

The color grade may be derived from the values X, Y and Z by using a comparison table which shows the known color grades of a number of diamonds. More preferably, chromaticity coordinates x and y should be derived from the values X, Y and Z by the following equations (IV) and (V):

$$x = X/(X + Y + Z) \qquad (IV)$$

$$y = Y/(X + Y + Z) \qquad (V)$$

Then, the coordinates x and y should be plotted on a chart sheet on which there are printed chromaticity coordinate areas that correspond to the known color grades of a number of diamonds.

The apparatus for measuring diamond colors according to the present invention is of great practical advantage in that it can objectively measure the colors of brilliant-cut diamonds, and can produce measured outputs which can easily be converted to color grades of the type which have been widely used conventionally.

BRIEF DESCRIPTION OF THE INVENTION

DESCRIPTION OF THE PREFERRED EMBODIMENTS

Figure 1:
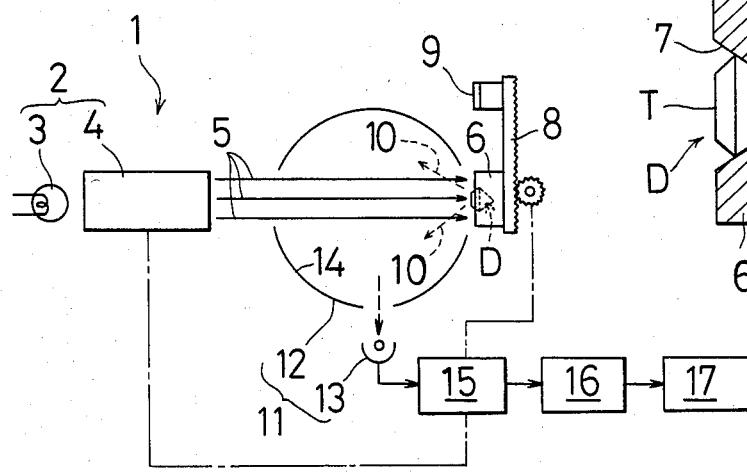
FIG. 1 is a schematic view, partly in block form, of an apparatus for measuring diamond colors according to an embodiment of the invention.

FIG. 1 shows an apparatus 1 for measuring diamond colors according to an embodiment of the present invention. The apparatus 1 includes a light source 2 having a halogen lamp 3 and a monochromator 4 for directly irradiating the whole area of a table facet side of a brilliant-cut diamond D with a beam 5 of monochromatic light at an angle (90~80 degrees) substantially normal to the table facet.

Figure 2:
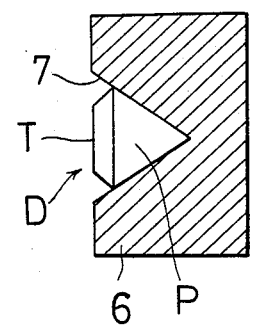
FIG. 2 is a cross-sectional view of a diamond holder in the apparatus shown in FIG. 1.

As illustrated in FIGS. 1 and 2, the diamond D is supported on a holder 6 with the pavillion P of the diamond received complementarily in a conical recess 7 in the holder 6. The holder 6 is in the form of a white plate made of ceramics. The table facet of the diamond D is designated at T. The holder 6 is affixed to a movable base 8 of a rack-and-pinion mechanism. A standard white plate 9 is also secured to the movable base 8 in spaced relation to the holder 6.

The apparatus 1 also comprises a photodetector 11 including an integrating sphere 12 which is about 200 mm across, and a multiplier phototube 13. The photodetector 11 serves to integrally detect a light 10 which has emerged from the diamond D through the table facet side and which has reached the multiplier phototube 13 through the integrating sphere 12 in which the light is reflected by an through surface 14.

A measurement unit 15 serves to control the monochromator 4 to change the wavelength of the monochromatic light beam 5 in the range of from about 380 to 780 nm, and to produce a spectrum of the light from the diamond D based on detected data from the photodetector 11. The measurement unit 15 also acts to calibrate the detected data by controlling the movable base 8 and measuring the standard white plate 9 instead of the diamond D.

The measurement unit 15 delivers data on the spectrum to an arithmetic unit 16. The measurement unit 15 and the arithmetic unit 16 should preferably be in the form of a microcomputer.

The arithmetic unit 16 serves to derive tristimulus values X, Y and Z from the spectrum produced by the measurement unit 15 based on the following arithmetic operations:

$$X = K \int \psi(\lambda) \bar{X}(\lambda) d\lambda \quad \text{(I)}$$

$$Y = K \int \psi(\lambda) \bar{Y}(\lambda) d\lambda \quad \text{(II)}$$

$$Z = K \int \psi(\lambda) \bar{Z}(\lambda) d\lambda \quad \text{(III)}$$

where $\psi(\lambda)$ is the spectrum, $\bar{x}(\lambda)$, $\bar{y}(\lambda)$ and $\bar{z}(\lambda)$ are the color matching functions, and K is a constant for equalizing Y to the amount of the measured light.

The tristimulus values X, Y and Z obtained by the arithmetic unit 16 are compared with a color grade table which shows the known estimated color grades of diamonds, so that the color grade of the diamond D can objectively be determined. For easier determination of the color grade, the arithmetic unit 16 further effects the following arithmetic operations to derive chromaticity coordinates x and y from the tristimulus values X, Y and Z:

$$x = X/(X+Y+Z) \quad \text{(IV)}$$

$$y = Y/(X+Y+Z) \quad \text{(V)}$$

Figure 3:
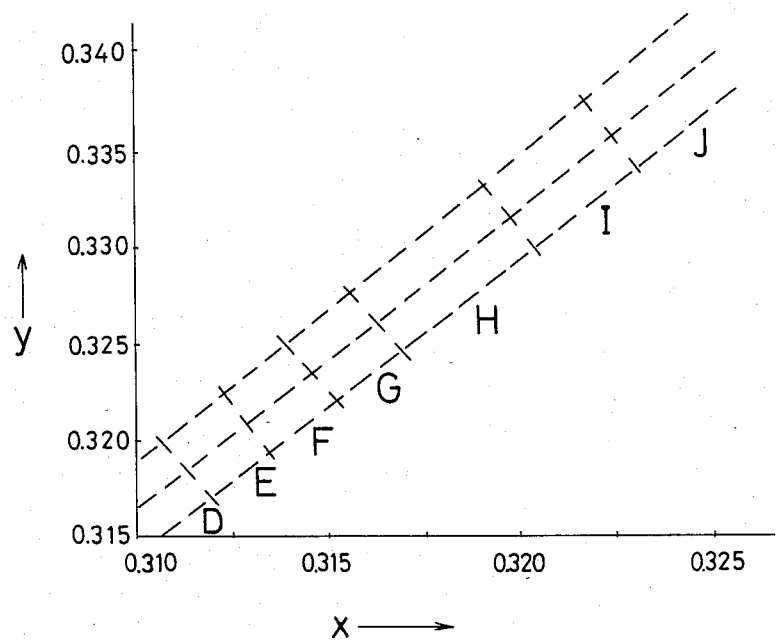
FIG. 3 is a view of a chart sheet used in the apparatus shown in FIG. 1.

Then the chromaticity coordinates x and y are supplied as inputs to a plotter 17 to put down a coordinate point on a chart sheet as shown in FIG. 3 which is set in the plotter 17.

Figure 4:
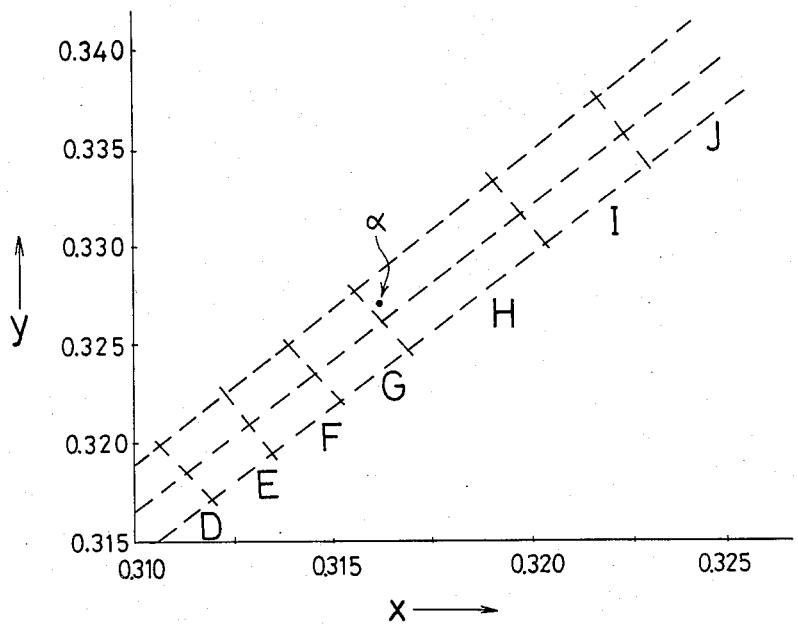
FIG. 4 is a view of a chart prepared by the apparatus of FIG. 1.

The operator can now have a chart as illustrated in FIG. 4. The coordinate point ($\alpha$) in the example shown is located in an area "H" near an area "G". Thus, the operator knows that the color grade of the diamond D is a grade "H" near a grade "G".

The chart sheet shown in FIG. 3 is prepared by measuring a number of diamonds on the apparatus 1 which have known color grades determined by the system of G.I.A. (Gemmological Institute of America), plotting a number of coordinate points thus obtained on a chromaticity diagram, thereby empirically preparing a scale (as shown by the dotted lines), and drawing such a scale on a coordinate system (as shown by the solid lines) which has been picked up from the chromaticity diagram. Therefore, the color grades are determined by the G.I.A. system.

Other color grade determinations include that which is carried out by the system of C.I.B.J.O. (International Confederation of Jewelry, Silverware, Diamonds, Pearls and Stones). With this system, a scale can be prepared in the manner described above, and such a scale is graduated on a transparent plate to thereby make a template. The color grade of the diamond can easily be determined in the other system by placing such a template on the diagram of FIG. 4.

Figure 5:
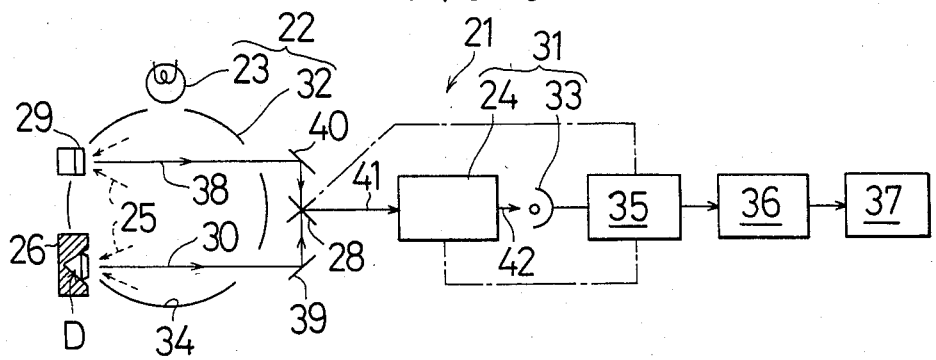
FIG. 5 is a schematic view, partly in block form, of an apparatus for measuring diamond colors according to another embodiment of the invention.

FIG. 5 illustrates an apparatus 21 for measuring diamond colors according to another embodiment of the present invention.

The apparatus 21 comprises a light source 22 which includes a xenon lamp 23 and an integrating sphere 32 for indirectly irradiating the table facet of a diamond D or a standard white plate 29 with white scattered light 25 via an inner surface 34 of the integrating sphere 32. The diamond D is supported on a holder 26 which is of the same construction as that of the holder 6 shown in FIG. 1.

A beam 30 of light which has emerged from the diamond D held by the holder 26 through the table facet, and another beam 38 of light which has reflected back from the standard white plate 29 are reflected respectively by mirrors 39, 40, and detected by a photodetector 31 via a sector mirror 28.

The photodetector 31 includes a diffraction grating monochromator 24 and a multiplier phototube 33 for selecting the wavelength of incident white light 41 and converting the same to a monochromatic light 42 for detection.

A measurement unit 35 serves to control the diffraction grating monochromator 24 to change the detected wavelength in the range of from about 380 to 780 nm, and also to control the sector mirror 28 for switching between the diamond D and the standard white plate 29 to produce a spectrum of the light beam from the diamond D.

An arithmetic unit 36 is similar to the arithmetic unit 16 shown in FIG. 1, and hence serves to derive tristimulus values X, Y and Z from the spectrum produced by the measurement unit 35. The arithmetic unit 36 also calculates chromaticity coordinates x and y and delivers them as outputs to a plotter 37 which is identical to the plotter 17 illustrated in FIG. 1.

The apparatus 21 thus enables the operator to determine the color grade of the diamond D on a chart as shown in FIG. 4.

With the apparatus 21, the diamond D is irradiated with white light, and hence with ultraviolet light having a wavelength of about 350 nm. Where the diamond D has fluorescence, the resultant spectrum is influenced by such fluorescence. About 1% of all diamonds is believed to have fluorescence.

The apparatus 1 and 21 may be modified in the following manner:

A. The monochromator 4 in the apparatus 1 may be dispensed with, and a monochromator may be positioned just in front of the phototube 13 for irradiating a diamond directly with white light. The lamp 23 in the apparatus 21 may be replaced with the light source 2 in the apparatus 1, and the monochromator 24 may be dispensed with for irradiating a diamond indirectly with monochromatic light.

B. Switching between the diamond D and the standard white plate 9 in the apparatus 1 may be carried out optically by a sector mirror instead of mechanically by the rack-and-pinion mechanism. The diamond D and the standard white plate 29 in the apparatus 21 may be measured alternately by a mechanical switching device such as a rack-and-pinion mechanism instead of optically by a sector mirror.

Figure 8:
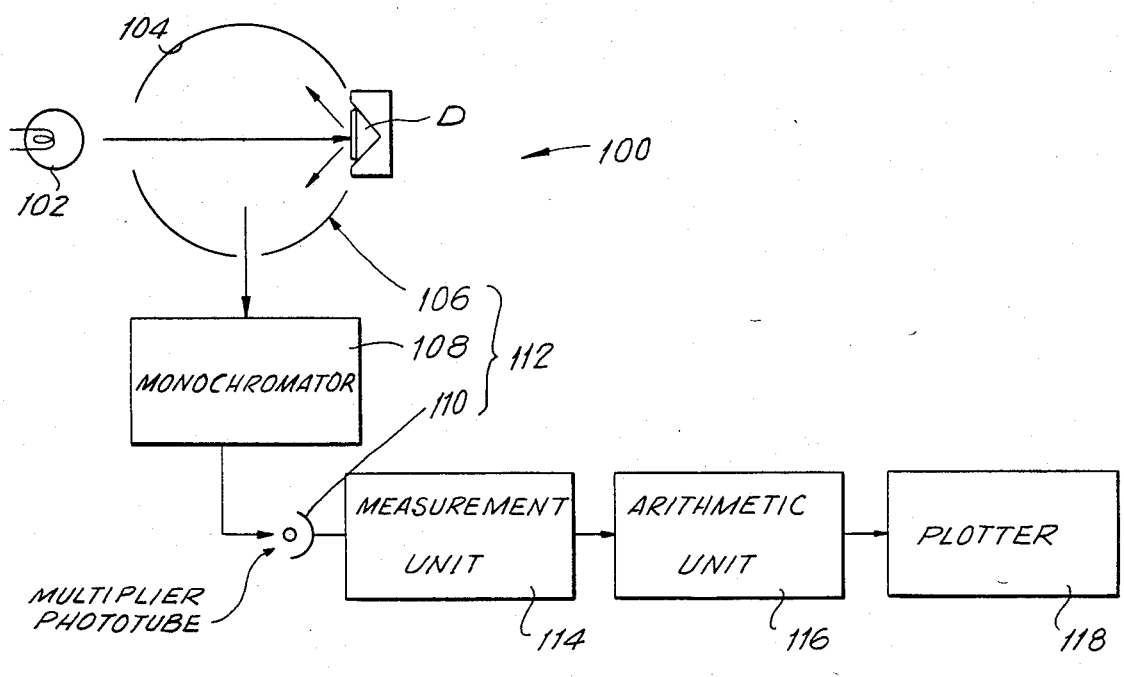
FIG. 8 is a schematic view, partly in block form, of an apparatus for measuring diamond colors according to another embodiment of the invention.

Yet another embodiment of the invention, designated by the general reference numeral 100, is illustrated in FIG. 8. Apparatus 100 includes a light source 102 which may comprise a xenon lamp or the like. Lamp 102 directly irradiates with light the table facet of a diamond D. Light reflected from the diamond is then reflected via the inner surface 104 of an integrating sphere 106 and received by a monochromator 108. Monochromator 108 directs the wavelength-selected light output therefrom to a photomultiplier tube 110. The integrating sphere 106, monochromator 108 and photomultiplier tube 110 together comprise a photodetector 112 for detecting the beam of white light reflected from the diamond and selecting therefrom a monochromatic light for detection.

As in the earlier-described embodiments, the output of photomultiplier 110 is received by a measurement unit 114 and, thereafter, by an arithmetic unit 116 for deriving the tristimulus values X, Y and Z. The outputs of unit 116 may be delivered to a plotter 118.

It should be evident to those skilled in the art that each of the elements and components of apparatus 100 may generally conform to and be constructed in accordance with the corresponding elements described in connection with the other embodiments herein described.

Figure 6:
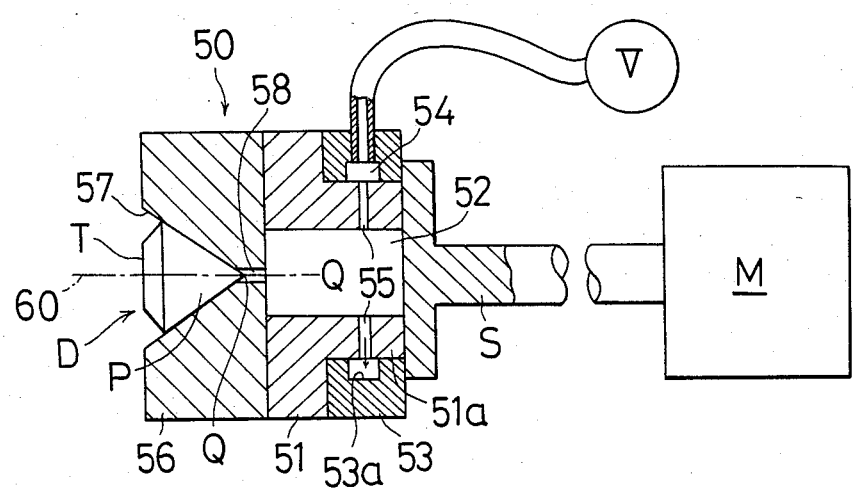
FIG. 6 is a cross-sectional view of a rotatable diamond holder.

FIG. 6 is illustrative of a rotatable holder 50 according to still another embodiment of the invention. The rotatable holder 50 comprises a rotatable base 51 driven by a motor M and a holder 56 mounted on a front face of the rotatable base 51, the holder 56 being of the same construction as that of the holders 6, 26 of the preceding embodiments. The rotatable holder 50 is rotatable about an axis 60 which passes through the center of the table T and culet Q of a diamond D supported on the holder 56.

The diamond D is retained on the holder 56 under a vacuum developed in a suction hole 58 defined through the bottom of a conical recess 57 and communicating with a cavity 52 in the rotatable base 51. The rotatable base 51 includes a barrel 51a around which there is fitted a fixed annular ring 53 having an inner peripheral groove 53a, which serves to define an annular space 54 around the barrel 51a. The annular space 54 is held in communication with the cavity 52 through passages 55 and with a vacuum pump V. When the pump V is operated, a vacuum is developed in the suction hole 58, the space 52, the passages 55, and the space 54 to attract and retain the diamond D in the conical recess 57. The rotatable holder 50 may be used in an apparatus for measuring diamond colors which is of the same structure as that of the apparatus 1, 21 except for the holders 6, 26.

During measurement of diamond colors by the apparatus incorporating the rotatable holder 50, the diamond D as supported on the rotatable holder 50 is rotated about the axis 60 which passes through the center of the table T and the culet Q of the brilliant-cut diamond D. The spectrum of the light reflected from within the diamond D being rotated has smaller irregularities for improved measurement accuracy.

Figure 7:
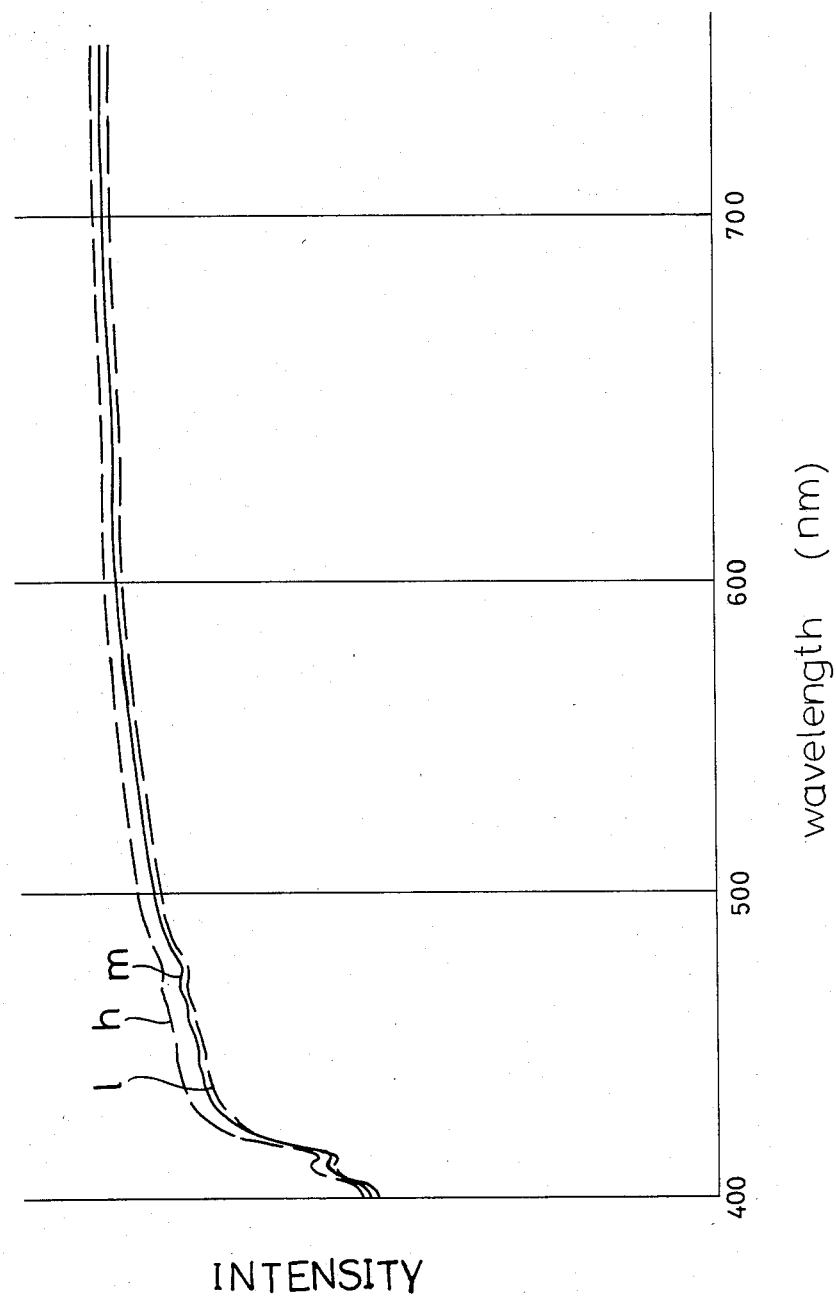
FIG. 7 is a diagram showing for comparison the spectrums of lights that have passed through a fixed diamond and a rotating diamond.

FIG. 7 shows spectrums l and h of lights which have come from a fixed diamond D, and a spectrum m of a light from the same diamond D when rotated about its axis at 1,000 r.p.m.. With the diamond D fixed in position, measured values tend to vary dependent on the orientation of the diamond D. For example, the spectrum may be at minimum as shown by l, and at maximum as shown by h. Measured values are on the average when the diamond is in rotation during measurement.

The reason why measured values vary with the orientation of the diamond D as fixed appears to be that the diamond D is not completely symmetrical, and the integrating sphere is not completely spherical.

The diamond D may be oriented in different directions on the fixed holder to obtain various measured values, which are then averaged. The results can therefore be the same as those obtained from a diamond supported on the rotatable holder 50. The fixed holder is more advantageous from the standpoint of complexity of the apparatus, and the rotatable holder is better from the standpoint of shortening measuring times.

Since the above as well as other modifications and changes are intended to be within the scope of the present invention, the foregoing description should be construed as illustrative and not in the limiting sense, the scope of the invention being defined by the appended claims.

What is claimed is:

1. An apparatus for measuring the color of a brilliant cut diamond comprising:

a light source for providing a measuring light;

a rotatable diamond holder comprising a rotatable base, a holder mounted on said base and including a conical recess defined in said holder for receiving the pavillion of a diamond to be measured and a suction hole extending from said recess, a motor operable for driving said rotatable base, and a vacuum pump, said base having a cavity communicating with said holder suction hole and said vacuum pump so that the pavillion of a diamond received in said conical recess is retained on said operatively rotatable holder under suction generated by said vacuum pump;

a photodetector including a monochromator and a photosensor for detecting a beam of light from the diamond as monochromatic light;

an integrating sphere in one of said light source and said photodetector;

a measurement unit for controlling the monochromator and the photosensor to obtain a spectrum of said detected light; and an arithmetic unit for deriving tristimulus values X, Y and Z from the measured spectrum.

2. An apparatus according to claim 1, wherein said light source comprises a lamp for irradiating the diamond directly with white light, and said photodetector comprises the integrating sphere, the monochromator, and the photo sensor for detecting light from the diamond as monochromatic light indirectly via an inner surface of said integrating sphere and with said monochromator.

3. An apparatus according to claim 1, wherein said light source comprises a lamp for providing white light and the integrating sphere arranged for irradiating the diamond indirectly with white light via an inner surface of said integrating sphere, and said photodetector comprises the monochromator and the photo sensor for detecting a beam of light from the diamond as monochromatic light directly with said monochromator.

* * * * *

UNITED STATES PATENT AND TRADEMARK OFFICE
CERTIFICATE OF CORRECTION

PATENT NO. : 4,508,449
DATED : April 2, 1985
INVENTOR(S) : Okazaki

It is certified that error appears in the above—identified patent and that said Letters Patent is hereby corrected as shown below:

Column 3, line 45: change "through" to --inner--.

Column 6, line 39: cancel "m of a" should read --m of--.

Signed and Sealed this

Seventh Day of January 1986

[SEAL]

Attest:

Attesting Officer

DONALD J. QUIGG

Commissioner of Patents and Trademarks